Dec. 5, 1950 F. H. HOWARD Plant Pat. 996
ROSE PLANT
Filed Dec. 12, 1949
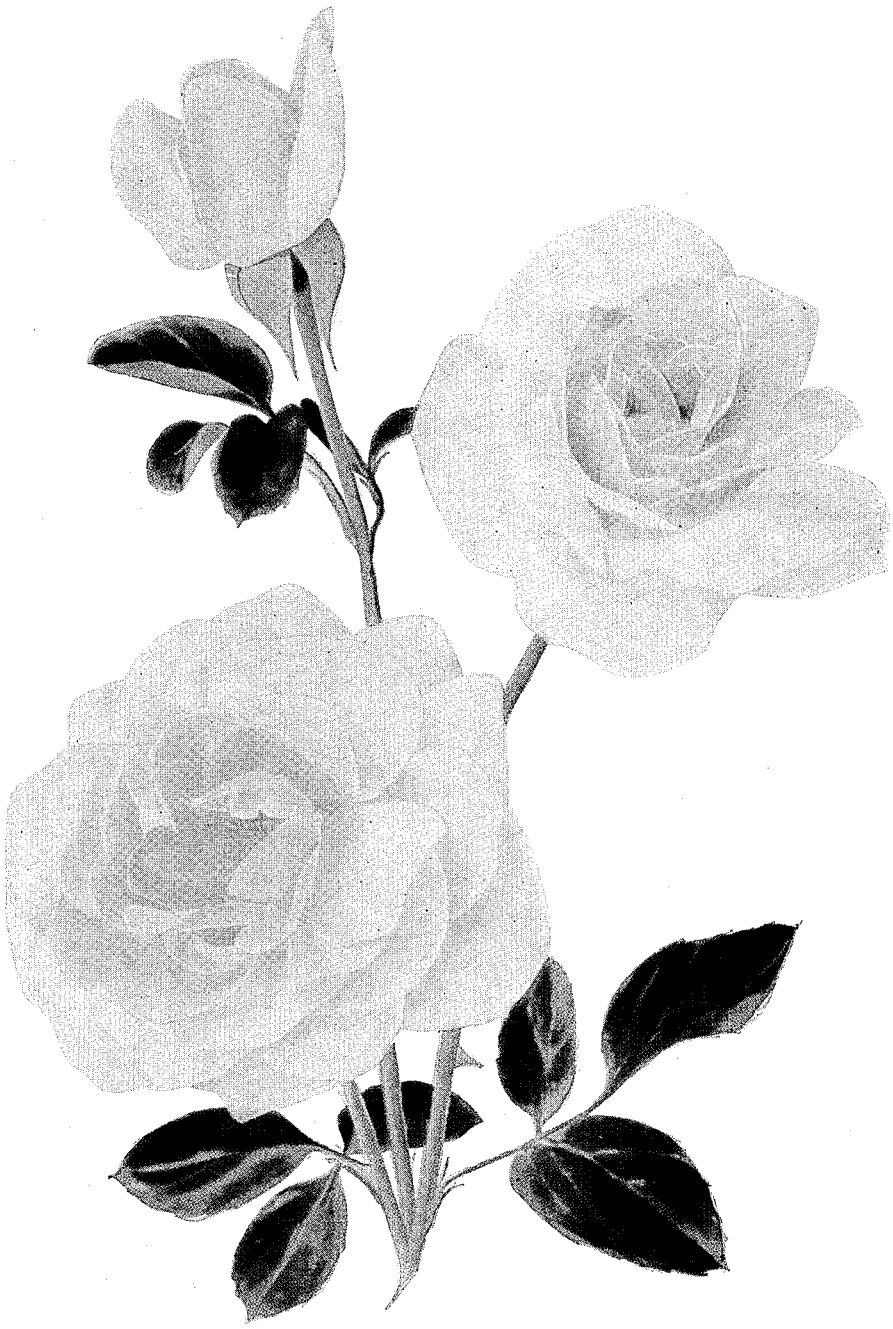
INVENTOR
Fred H. Howard, deceased
By Minnie J. Howard, Executrix
By Orvella M. Kile
Plant Pat. Agt.

Patented Dec. 5, 1950

Plant Pat. 996

UNITED STATES PATENT OFFICE

996

ROSE PLANT

Fred H. Howard, deceased, late of Montebello, Calif., by Minnie J. Howard, executrix, Montebello, Calif., assignor to Howard & Smith, Montebello, Calif.

Application December 12, 1949, Serial No. 132,506

1 Claim. (Cl. 47—61)

The present invention pertains to a new variety of hybrid tea rose plant, originating from a cross between the variety Los Angeles (unpatented) and an unnamed seedling. It is a particularly strong and vigorous grower and prolific bloomer for its color class, and possesses other desirable qualities which in combination make it an outstanding rose. Its rich green foliage is of immense size and unusual rounded shape—no rose known to me equals its foliage in texture and vigor. Its stems are very long, it being not unusual at all for them to be 24 to 30 inches in length.

This new variety was originated in gardens in Montebello, California, and has been reproduced at the same location by means of budding. Its characteristic features appear to be permanent.

Illustrations accompanying these specifications show three specimens of the flower of this new variety in various stages of opening, together with portions of the stem and foliage.

In the following detailed description, color plate numbers refer to Ridgway's Color Standards and Nomenclature. Other color terminology refers to the ordinary dictionary meaning.

*The plant*

Growth: Upright bush; very vigorous, growing to five or six feet in height when mature.

Blooming habit: A continuous and exceedingly free bloomer. A three-year-old plant easily produces 350 flowers per year.

Foliage: Pinnately compound, with 3 to 5 leaflets.

*Quantity.*—Average in quantity but appears abundant because of the large size.

*Size.*—Very large. Terminal leaflet averages about 3 inches long by 2½ inches wide.

*Shape.*—Almost round, base and apex both being rounded. This shape is rather unusual in rose foliage, although not unknown.

*Color.*—Dark rich green.

*Texture.*—Heavy and leathery. Foliage is very strong and does not easily wilt.

*Midribs.*—Prominent and strong.

*Disease resistance.*—Excellent. Variety has never been found to have any of the diseases commonly afflicting rose foliage.

*Stipules.*—Prominent, broad and clinging.

Stems:

*Strength.*—Very strong and sturdy.

*Length.*—Frequently 24 to 30 inches long.

*Thorns.*—Numerous; approximately ¼ inch long; extend at right angles to stem; usually red.

*Color.*—Sea green.

*The flower*

Bud:

*Size.*—Long, measuring about 1½ inches.

*Shape.*—Ovoid; long-pointed.

*Color.*—Coral pink.

*Peduncle.*—Short; rigid.

*Calyx.*—Simple.

*Sepals.*—Prominent, simple; 1½ inches long; reflex early and clasp stem.

*Ovary.*—Small; partially enclosed.

Bloom:

*Size.*—Medium to large; average diameter is 4 to 4½ inches.

*Petalage.*—35 to 40 petals.

*Form.*—High-centered, opening into loose cupshape.

*Color.*—General color effect is that it is two-toned with the center coral pink and the outside petals shell pink in the open bloom.

Petals:

*Size.*—Average 1¾ inches by 2 inches. Oval to obovate; edge smooth. Edges do not roll and petal reflexes only slightly.

*Longevity.*—Keeping qualities very good.

*Fragrance.*—Slight tea fragrance.

*Texture.*—Thick and substantial. Stands up in the hottest sun without shrivelling.

*Persistence.*—Clinging.

Reproductive organs:

*Pistils.*—Many; tightly bunched. *Style*—prominent; light yellow.

*Anthers.*—Numerous; surround pistils; light yellow.

*Comparison*

The varieties most nearly like this new variety are Anzac (Plant Patent No. 636) and Apricot Queen (Plant Patent 464), the similarity being mostly in the color of the flower. Although its flower color is similar to that of Anzac, this new variety differs particularly in the shape of its bud which is longer and more pointed and in the quantity of good flowers produced. Anzac has been known as a very free bloomer but this new variety produces at least three times as many blooms. Also this variety's stems are much longer, the growth much stronger and more vigorous, the foliage darker, more substantial, much larger and of a different shape, and the flower petals are more substantial.

Having thus disclosed this invention, it is claimed:

The new and improved variety of hybrid tea rose plant, substantially as herein shown and described, characterized particularly by its very strong and vigorous growth; its exceedingly prolific production of good flowers; its very large, dark green, substantial, disease-resistant foliage, with unusual rounded leaflets; its long, sturdy flower stems; its long, pointed bud; and the substantial petals of its flowers.

MINNIE J. HOWARD,
*Executrix of the Last Will and Testament of Fred H. Howard, Deceased.*

No references cited.